United States Patent [19]

Phillips et al.

[11] Patent Number: 5,186,715
[45] Date of Patent: Feb. 16, 1993

[54] BILIARY DRAINAGE METHOD

[75] Inventors: David Phillips, Boston, Mass.; William M. Appling, Hartford, N.Y.

[73] Assignee: E-Z-EM, Inc., Westbury, N.Y.

[21] Appl. No.: 622,977

[22] Filed: Dec. 6, 1990

[51] Int. Cl.⁵ .............................................. A61M 1/00
[52] U.S. Cl. ........................................ 604/28; 604/27; 604/43
[58] Field of Search ...................... 604/27, 28, 36, 39, 604/43, 410, 183, 185, 264, 284

[56] References Cited

U.S. PATENT DOCUMENTS

| | | | |
|---|---|---|---|
| 3,672,372 | 6/1972 | Heimlich | 604/54 |
| 4,098,275 | 7/1978 | Consalvo | 604/27 |
| 4,608,043 | 8/1986 | Larkin | 604/410 |
| 4,692,141 | 9/1987 | Mahurkar | 604/43 |
| 4,722,725 | 2/1988 | Sawyer et al. | 604/27 |
| 4,808,156 | 2/1989 | Dean | 604/43 |
| 5,064,415 | 11/1991 | Walder et al. | 604/171 |

FOREIGN PATENT DOCUMENTS 1025432  6/1983  U.S.S.R. ................................. 604/27

Primary Examiner—John J. Wilson
Attorney, Agent, or Firm—McAulay Fisher Nissen Goldberg & Kiel

[57] ABSTRACT

A drainage system for draining bile is provided. The drainage system includes an elongated drainage catheter with distal segment and a proximal segment. The catheter includes a first lumen which extends longitudinally through at least a portion of the distal catheter segment and longitudinally through the entire length of the proximal segment. The catheter also includes a second lumen which extends longitudinally solely through at least a portion of the proximal catheter segment. The system includes a drainage bag adapted for connection to the proximal segment to the drainage catheter. A one-way valve is associated with a drainage bag to allow bile to enter into the bag through the second lumen and to exit from the bag into the first lumen.

1 Claim, 2 Drawing Sheets

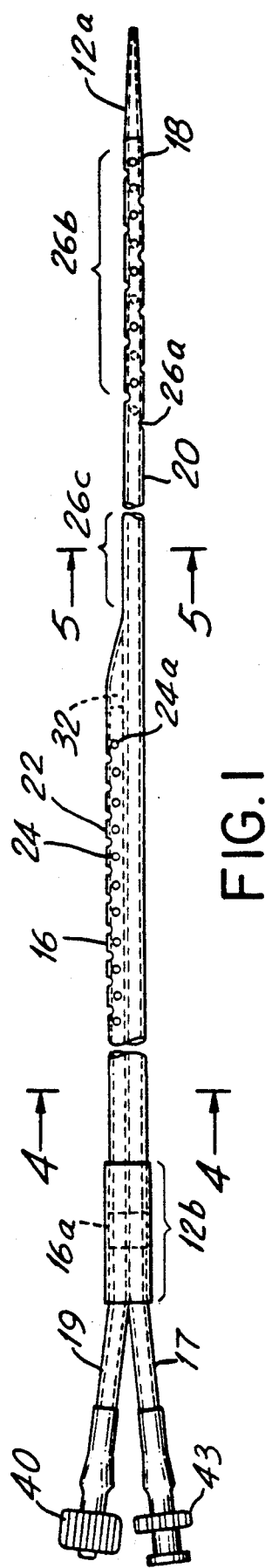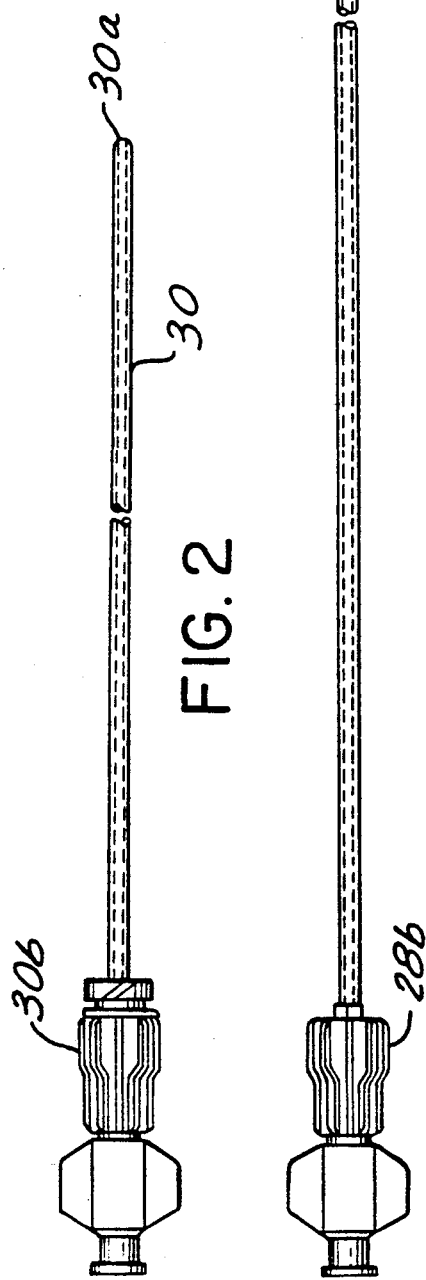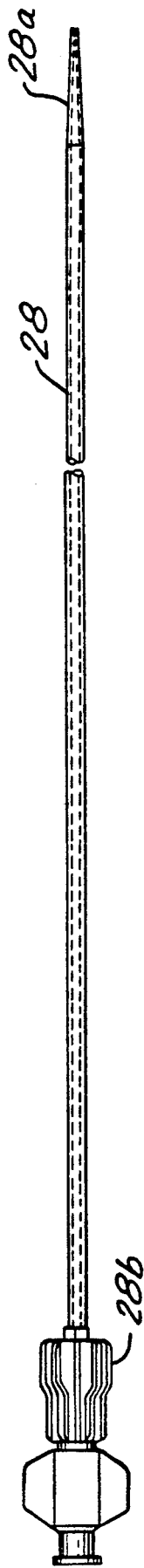

5,186,715

BILIARY DRAINAGE METHOD

BACKGROUND OF THE INVENTION

The present invention relates to a drainage system for biliary drainage and more particularly relates to such a system which allows drained bile to be returned to the duodenum when needed.

The excretory apparatus of the liver includes the hepatic duct, the gallbladder, the cystic duct, and the common bile-duct which is formed by the junction of the hepatic and cystic ducts.

Bile is secreted by the cells of the liver into the common bile duct which drains into the duodenum. Between meals the duodenal orifice of the duct is closed and instead of flowing into the duodenum bile flows into the gallbladder where it is stored. When food enters the mouth, the duodenal orifice opens, and when the gastric contents enter the duodenum the gallbladder contracts so that the bile enters into the duodenum where it is used in the digestive process to help digest fats.

Certain patients need biliary drainage. This drainage is needed by some patients on a temporary basis and in other patients biliary drainage is needed permanently. Biliary drainage may be accomplished using either an external or an internal drainage system. Although internal systems have certain advantages their proper functioning is not easily verified. Further internal drainage systems sometimes allow bowel contents to be reflexed back into the biliary system with concommitant complications. Although bile is needed for proper food digestion, no existing drainage system, internal or external, allows bile to be available in the duodenum when needed to help in the digestion of fats.

Accordingly, it is an object of the present invention to provide a biliary drainage system whose functioning can be easily verified.

It is another object of the present invention to provide such a system which prevents inadvertent reflux of bowel contents into the biliary system.

Yet a further object of the present invention is to provide such a system which allows bile to be available in the duodenum when needed for proper digestion.

Yet a further object of the present invention is to provide such a system which is relatively inexpensive to manufacture and safe to use.

BRIEF DESCRIPTION

In brief the present invention relates to a biliary drainage system which provides for external and internal drainage of bile. The biliary drainage system includes a drainage catheter having a distal segment and an proximal segment. A first lumen is formed in the catheter. The first lumen extends longitudinally through at least a portion of the distal catheter segment and throughout the length of the proximal catheter segment. A second lumen is formed in the catheter. The second lumen extends longitudinally solely within a portion of the proximal segment of the catheter. The second lumen does not extend into the distal catheter segment. The drainage system includes a drainage bag with two one-way valves. The one-way valves, in conjunction with the first and second catheter lumens, allows bile to enter into the bag through the second lumen and to exit from the bag, into the duodenum, through the first lumen.

BRIEF DESCRIPTION OF THE DRAWINGS

FIG. 1 is side elevational view of the catheter of the biliary drainage device of the present invention.

FIG. 2 is a view of one obturator of the biliary drainage device of the present invention.

FIG. 3 is a view of a second obturator.

DESCRIPTION OF THE PREFERRED EMBODIMENT

Figures 4, 5:
FIG. 4 is a sectional view taken generally along line 4—4 of FIG. 1.
FIG. 5 is a sectional view taken generally along line 5—5 of FIG. 1.
Figure 6:
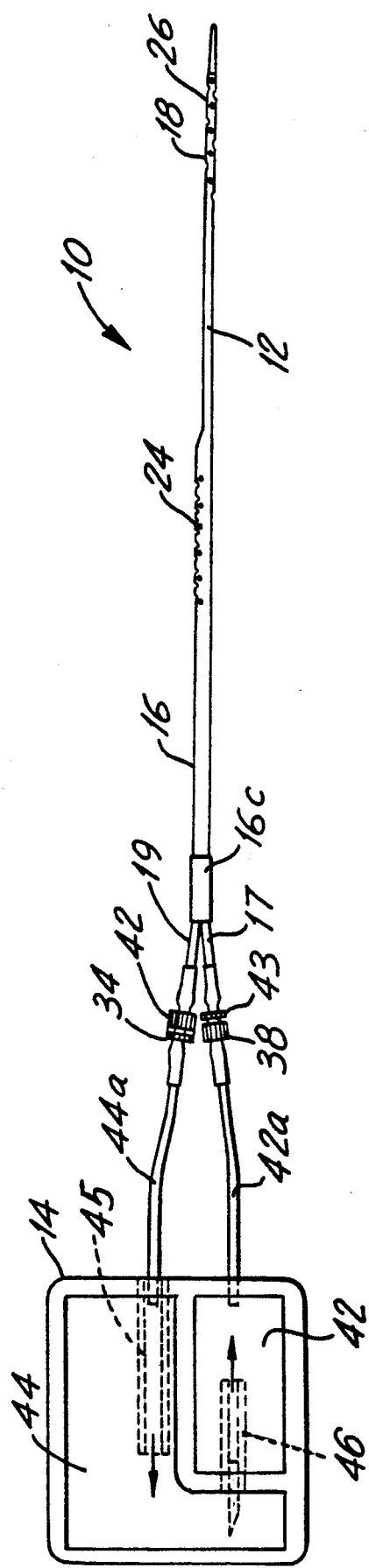
FIG. 6 is a side elevation view of the biliary drainage device of the present invention showing the catheter connected to the drainage bag.

Referring now to the drawings, and more particularly to FIG. 6, the reference numeral 10 denotes notes the drainage system of the present invention. Drainage system 10 is used for biliary drainage.

Drainage system 10 includes a drainage catheter 12 and a drainage bag 14. Drainage catheter 12 has a proximal segment 16 and a distal segment 18. At its proximal end 16a, proximal segment 16 bifurcates into two separate catheter portions 17, 19.

Drainage catheter 12 is formed with a first lumen 20 which extends longitudinally through the entire proximal segment 16 and through at least a portion of the distal segment 18. Drainage catheter 12 is formed with a second lumen 22 which extends longitudinally through at least a portion of the proximal catheter segment 16. The second lumen 22 does not extend into the distal segment 18. First lumen 20 terminates into catheter portion 17. Second lumen 22 terminates in catheter portion 19.

The proximal segment 16 of catheter 12 is formed with a plurality of drainage holes 24 which are in communication with the second lumen 22. The distal segment 18 of catheter 12 is formed with a plurality of holes 26 which are in communication with the first lumen 20.

A first obturator 28 is associated with the first lumen 20 and a second obturator 30 is associated with the second lumen 22. Obturators 28, 30 are shaped and dimensioned to be removably received in lumens 20, 22 and are used to place of the catheter properly in a patient. In a preferred embodiment obturators 28, 30 are made of teflon. In the preferred embodiment obturator 28 is formed with a tapered tip 28a, the taper of tip 28a matching the taper of catheter tip 12a. Obturator 30 is formed with a blunt tip 30a.

In use catheter 12 is positioned such that drainage holes 26 are in a patient's duodenum and drainage holes 24 are in the patient's common bile duct. Holes 24 and 26 are spaced from one another in a manner to permit this. A radio opaque marker 32, which is seated in the distal end of second lumen 22, helps in proper placement of the catheter. In the preferred embodiment the distal most hole 24a of the holes associated with second lumen 22 is longitudinally spaced from the proximal most hole 26a associated with first lumen 20, about thirteen (13) centimeters.

In a preferred embodiment of the invention the distal segment 18 of catheter 12 is about seventeen (17) centimeters in length which includes a tapered tip 12a having a length of about two (2) centimeters, and a hole containing segment 26b having a length of about five (5)

centimeters. The proximal segment 16 of catheter 12 is about twenty (20) centimeters in length and includes a transitional segment 16a having a length of about one (1) centimeter and a hole containing segment 24b having a length of about five (5) centimeters. Catheter 12 includes proximal end 12b having a length of about 2.54 centimeters which terminates in catheter portions 17, 19 with each having a length of about 3.75 centimeters. In the preferred embodiment catheter 12 is made of urethane.

Drainage bag 14 is formed with a first bag segment 42. First bag segment 42 includes a connector portion 42a which is attachable to catheter portion 17. A second bag segment 44 includes a connector portion 44a which is attachable to catheter portion 19. Connector portions 42a and 44a as well as catheter portions 17, 19, are formed with polarized locking segments 34, 38, 40, 43 to insure that the connector portions are not inadvertently connected to the wrong catheter portions. The obturators 28, 30 are also provided with appropriate locking segments 28b, 30b to allow the obturators to be securely connected to the catheters. Bag segment 44 is provided with a one-way reed valve 45; bag segment 42 is provided with a one-way reed valve 46.

When catheter 12 is properly placed in a patient's body, drainage system 10 works as follows. Bile from the common bile duct drains into second lumen 22 through holes 24. The bile is then collected in second bag segment 44. Due to valve 46 the bile can flow from bag segment 44 to bag segment 42. However material in bag segment 42 cannot return to bag segment 44. Accordingly when a patient eats and it is desired to have bile present in the duodenum to aid in fat digestion the patient squeezes bag 14 pushing bile from bag segment 44 into bag segment 42. From the bag segment 42 this bile flows into first lumen 20 and out of holes 26 and into the duodenum where it can be used by the body in the digestive process. Because of valves 45 and 46 material from the duodenum cannot inadvertently reflux through drainage system 10 into the biliary system. In the preferred embodiment bag 14 is made of polyvinyl chloride. Bag 14 is about 4¼" in length and 4½" in width. Bag segment 44 is about 3¾ ID in length and 2¼ ID in width. Bag segment 42 is about 2⅝ ID in length and 1½ ID in width. Bag 14 can hold about 80 ccs.

In use drainage system 10 provides a safe and efficient method of biliary drainage which permits, on demand, profusion of bile for use in digestion. The drainage system 10 allows for easy verification of its functioning and further prevents inadvertent contamination of the biliary system with bowel contents.

What is claimed is:

1. A method of biliary drainage comprising the steps of:

placing a catheter having first and second lumens each provided with associated holes in a patient such that said first lumen terminates at its distal end, in the patient's duodenum and said second lumen terminates, at its distal end, in the patient's common bile duct;

connecting the catheter to a drainage bag having first and second segments, said first segment of the drainage bag being connected to said first catheter lumen and said second segment of the drainage bag being connected to said second catheter lumen;

providing the first bag segment with a one-way valve to allow material to flow from said second segment to said first segment while preventing the flow of material from said first segment to said second bag segment;

collecting bile from the patient's common bile duct through the associated holes in said second lumen through said second lumen and into the second bag segment;

providing bile, on demand, to the patient's duodenum by squeezing the drainage bag causing bile to flow from said second segment to said first segment, into said first lumen and through its associated holes.

* * * * *